United States Patent
Endo et al.

(10) Patent No.: US 7,189,550 B2
(45) Date of Patent: Mar. 13, 2007

(54) β1,3-GALACTOSYLTRANSFERASE AND DNA ENCODING THE SAME (75) Inventors: Tetsuo Endo, Palo Alto, CA (US); Satoshi Koizumi, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 11/227,177

(22) Filed: Sep. 16, 2005

(65) Prior Publication Data

US 2006/0014262 A1    Jan. 19, 2006

Related U.S. Application Data

(62) Division of application No. 10/475,587, filed as application No. PCT/JP02/04034 on Apr. 23, 2002, now Pat. No. 6,974,687.

(30) Foreign Application Priority Data

Apr. 23, 2001  (JP)  ............... P.2001-123864

(51) Int. Cl.
*C12N 15/54* (2006.01)
*C12N 9/10* (2006.01)
*C12N 1/15* (2006.01)
*C12N 1/19* (2006.01)
*C12N 1/21* (2006.01)

(52) U.S. Cl. .............. 435/193; 435/71.2; 435/72; 435/74; 435/320.1; 435/252.3; 435/252.33; 536/23.2; 536/23.7

(58) Field of Classification Search ................ 435/193, 435/252.3, 320.1, 252.33, 72, 74, 69.1, 71.2, 435/325; 536/23.2, 23.7
See application file for complete search history.

(56) References Cited

U.S. PATENT DOCUMENTS 5,395,757 A    3/1995 Hayakawa et al. ........... 435/84

FOREIGN PATENT DOCUMENTS

WO    WO 00/46379    8/2000

OTHER PUBLICATIONS

Amado et al. A Family of Human β-1, 3-galactosyltransferases vol. 273, No. 21, pp. 12770-12778. Journal of Biological Chemistry 1998.*

(Continued)

*Primary Examiner*—Kathleen M. Kerr
*Assistant Examiner*—Kagnew Gebreyesus
(74) *Attorney, Agent, or Firm*—Fitzpatrick, Cella, Harper & Scinto (57) ABSTRACT

The present invention provides a protein having β1,3-galactosyltransferase activity, a DNA encoding the protein, a transformant comprising the DNA, a process for producing the protein using the transformant, and a process for producing a galactose-containing complex carbohydrate using the transformant.

12 Claims, 1 Drawing Sheet

OTHER PUBLICATIONS

Hennet et al Genomic cloning and expression of three murine UDP-galactose:Beta-N-Acetylglucosamine beta1,3-galactosyltransferase genes. Journal of Biological Chemistry 1998 vol. 273, No. 1., pp. 58-65.*

Appelmelk et al. Phase variation in H type1 and Lewis A epitop og *Helicobacter pylori* Lipopolysaccharide. Infection and Immunity; vol. 68 No. 10, Oct. 2000., pp. 5928-5932.*

Appelmelk, et al., "Phase Variation in H Type I and Lewis a Epitopes of . . . ", *Infection and Immunity*, vol. 68, No. 10 (2000), pp. 5928-5932.

Tomb, et al., "The Complete Genome Sequence of the Gastric Pathogen *Helicobacter pylori*", *Nature*, vol. 388 (1997), pp. 539-547.

Gilbert, et al., "Biosynthesis of Ganglioside Mimics in *Campylobactoer jejuni* OH4384", *Jour. of Bio. Chem.*, vol. 275, No. 6 (2000), pp. 3896-3906.

Linton, et al., "Phase variation of a β-1,3 galactosyltransferase involved in generation . . . ", *Molecular Microbiology*, vol. 37, No. 3 (2000), pp. 501-514.

Bailly, et al., "Characterization and specific assay for a galactoside beta-3-galactosyltransferase of human kidney . . . " *Journal of Biochemistry*, vol. 173 (1988), pp. 417-422.

Basu SS, et al., "Purification and characterization of avian glycolipid: beta- galactosyltransferases (GaIT-4 and GaIT-3): cloning and . . . ", *Acta Biochim Pol.*, vol. 45, No. 2 (1998), pp. 451-467.

Gilbert, et al., "Biosynthesis of ganglioside mimics In *Campylobacter jejuni* OH4384, Identification of the . . . ", *J. Biol. Chem.*, vol. 275, No. 6 (2000), pp. 3896-3906.

Shib S. Basu et al., "Purification and Characterization of Avian Glycolipid: β- Galactosyltransferases (GaIT-4 and GaIT-3): Cloning and Expression of Truncated βGaIT-4", *Acta Biochmca Polonica*, vol. 45, No. 2, 1998, pp. 451-467.

Hiroshi Miyazaki et al., "Expression Cloning of Rat cDNA Encoding UDP-galactose:$G_{D2}$ β1,3- Galactosyltransferase That Determines the Expression of $G_{D1b}/G_{M1}/G_{A1}$", *The Journal of Biological Chemistry*, vol. 272, No. 40, Oct. 3, 1997, pp. 24794-24799.

Sujoy Ghosh et al., "Purification, Properties, and Immunological Characterization of GaIT-3 (UDP-galactose: GM2 Ganglioside, β1-3 Galactosyltransferase) From Embryonic Chicken Brain", *Glyconconjugate Journal*, vol. 12, No. 6, 1995, pp. 838-847.

Pascal Bailly et al., "Characterization and Specific Assay for a Galactoside β-3- Galactosyltransferase of Human Kidney", *Eur. Journal of Biochemistry*, vol. 173, Apr. 15, 1988, pp. 417-422.

* cited by examiner

β1,3-GALACTOSYLTRANSFERASE AND DNA ENCODING THE SAME

This application is a division of application Ser. No. 10/475,587 filed Apr. 28, 2004, now U.S. Pat. No. 6,974,687 issued Dec. 13, 2005, which in turn is a national stage application of PCT/JP02/04034, filed Apr. 23, 2002, which itself claims benefit of Japanese patent application No. 123864, filed Apr. 23, 2001.

TECHNICAL FIELD

The present invention relates to a protein having β1,3-galactosyltransferase activity, a DNA encoding the protein, a transformant comprising the DNA, a process for producing a protein having β1,3-galactosyltransferase activity using the transformant, and a process for producing a galactose-containing complex carbohydrate using the transformant.

BACKGROUND ART

β1,3-Galactosyltransferase genes, derived from mammals [Japanese Published Unexamined Patent Application No. 181759/94; *J. Biol. Chem.*, 272, 24794 (1997); *J. Biol. Chem.*, 273, 58 (1998); *Eur. J. Biochem.*, 263, 571 (1999); *J. Neurosci. Res.*, 58, 318 (1999)] and derived from a bird [*Acta Biochemica Polonica*, 45, 451 (1998)] have been obtained. However, there is no example in which β1,3-galactosyltransferase gene derived from an animal was expressed as an active protein in a microorganism such as *Escherichia coli*. Although there is an example in which the gene derived from a bird was expressed in *Escherichia coli* [*Acta Biochemica Polonica*, 45, 451 (1998)], its activity was very weak.

On the other hand, in the case of microorganisms, a β1,3-galactosyltransferase gene has been obtained from *Campylobacter jejuni* and expressed in *Escherichia coli* as an active protein [*J. Biol. Chem.*, 275, 3896 (2000); *Mol. Microbiol.*, 37, 501 (2000)]. However, as the substrate of the protein, the references describe only GalNAcβ1,4[NeuAcα2,3]Galβ1,4Glc-FCHASE in which its non-reducing terminal has N-acetylgalactosamine and its reducing terminal is labeled with a fluorescent material [FCHASE (6-(5-fluoresceincarboxamido)hexanoic acid succimidyl ester)], and the references do not describe a complex carbohydrate having a modification on its reducing terminal or a complex carbohydrate having N-acetylglucosamine on its non-reducing terminal.

Regarding *Helicobacter pylori* 26695, the full nucleotide sequence of its genomic DNA has been determined [*Nature*, 388, 539 (1997)], but a gene product which functions as a β1,3-galactosyltransferase has not been known. Furthermore, since a Galβ1,3GlcNAc structure in *Helicobacter pylori* disappeared by disruption of a gene which corresponds to HP0619 gene of *Helicobacter pylori* 26695, BP0619 gene is expected to be a β1,3-galactosyltransferase gene [*Infect. Immun.*, 68, 5928 (2000)], but there have been neither examples in which the gene was expressed in a microorganism such as *Escherichia coli* nor descriptions regarding its detailed enzyme activity.

Among galactose-containing complex carbohydrates, complex carbohydrates having a Galβ1,3-R structure in the skeleton are particularly important as synthesis intermediates of Lewis$^a$ or Lewis$^b$ which is a blood group complex carbohydrate [*J. Pediatr. Gastroenterol. Nutr.*, 30, 181 (2000)], and is contained in human milk in a large amount and considered to have a preventive effect against bacterial infection [*Anal. Biochem.*, 2239, 218 (1994); *J. Chromatogr.*, 685, 211 (1996); *Lancet*, 347, 1017 (1996)].

For the production of the galactose-containing complex carbohydrates having a Galβ1,3-R structure, an extraction method from human milk [*Carbohydr. Res.*, 178, 79 (1988)], a chemical synthesis method [*Carbohydr. Res.*, 316, 121 (1999)] and the method using an enzyme [*Glycoconjugate J.*, 16, 189 (1999)] have been reported, however, each of the methods has problems from the viewpoints of cost and productivity, and thus an industrial production method has not been established yet.

DISCLOSURE OF THE INVENTION

Objects of the present invention are to provide a protein having β1,3-galactosyltransferase activity, a DNA encoding the protein, a transformant comprising the DNA, a process for producing a protein having β1,3-galactosyltransferase activity using the transformant, and a process for producing a galactose-containing complex carbohydrate using the transformant.

In order to solve the above problems, the present inventors have conducted intensive studies and obtained a DNA corresponding to HP619 gene from *Helicobacter pylori* NCTC 11637 based on the sequence information of *Helicobacter pylori* 26695 in which the sequence of the genomic DNA was determined. As a result of the activity measurement of the gene product, the present inventors found that the gene product has β1,3-galactosyltransferase activity, and thus the present invention has been completed.

Specifically, the present invention relates to the following (1) to (17):

(1) A protein comprising the amino acid sequence represented by SEQ ID NO:1.

(2) A protein which consists of an amino acid sequence in which at least one amino acid is deleted, substituted, inserted or added in the amino acid sequence represented by SEQ ID NO:1, and has β1,3-galactosyltransferase activity.

(3) A protein which has a homology of at least 80% with a protein consisting of the amino acid sequence represented by SEQ ID NO:1, and has β1,3-galactosyltransferase activity.

(4) A DNA encoding the protein according to any one of (1) to (3).

(5) A DNA comprising the nucleotide sequence represented by SEQ ID NO:2.

(6) A DNA which hybridizes with a DNA consisting of the nucleotide sequence represented by SEQ ID NO:2 under stringent conditions, and encodes a protein having β1,3-galactosyltransferase activity.

(7) A recombinant DNA comprising the DNA according to any one of (4) to (6).

(8) A transformant comprising the recombinant DNA according to (7).

(9) The transformant according to (8), which is obtained by using a microorganism, a plant cell, an insect cell or an animal cell as a host cell.

(10) The transformant according to (9), wherein the microorganism belongs to the genus *Escherichia*.

(11) The transformant according to (10), wherein the microorganism belonging to the genus *Escherichia* is *Escherichia coli*.

(12) A process for producing a protein having β1,3-galactosyltransferase activity, which comprises: culturing the transformant according to any one of (8) to (11) in a medium to produce and accumulate a protein having β1,3-galactosyltransferase activity in the culture, and recovering the protein having β1,3-galactosyltransferase activity from the culture.

(13) A process for producing a galactose-containing complex carbohydrate, which comprises: allowing a culture of the transformant according to any one of (8) to (11) or a treated product of the culture as an enzyme source, uridine-5'-diphosphogalactose and an acceptor complex carbohydrate to be present in an aqueous medium to produce and accumulate the galactose-containing complex carbohydrate in the aqueous medium, and recovering the galactose-containing complex carbohydrate from the aqueous medium.

(14) The process according to (13), wherein the treated product of the culture is selected from the group consisting of a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells and an enzyme preparation obtained by extracting from the cells.

(15) The process according to (13), wherein the acceptor complex carbohydrate is a complex carbohydrate comprising an oligosaccharide having N-acetylglucosamine in its non-reducing terminal.

(16) The process according to (15), wherein the oligosaccharide having N-acetylglucosamine in its non-reducing terminal is selected from the group consisting of GlcNAc, GlcNAcβ1,3Galβ1,4Glc and GlcNAc 1,3Galβ1,4GlcNAcβ1,3Galβ1,4Glc.

(17) The process according to (13), wherein the galactose-containing complex carbohydrate is selected from the group consisting of lacto-N-biose (Galβ1,3GlcNAc), lacto-N-tetraose (Galβ1,3GlcNAcβ1,3Galβ1,4Glc) and paralacto-N-hexaose (Galβ1,3GlcNAcβ1,3Galβ1,4GlcNAcβ1,3Galβ1,4Glc).

The protein of the present invention is a protein having an activity of transferring galactose to an acceptor complex carbohydrate having N-acetylglucosamine in its non-reducing terminal via β1,3-linkage among proteins having β1,3-galactosyltransferase activity. The origin of the protein of the present invention is not limited, but is preferably a protein derived from a microorganism, more preferably a protein derived from a microorganism belonging to the genus *Helicobacter*, and most preferably a protein derived from a microorganism belonging to *Helicobacter pylori*. Specifically, the protein includes a protein comprising the amino acid sequence represented by SEQ ID NO:1 and a protein which consists of an amino acid sequence in which at least one amino acid is deleted, substituted, inserted or added in the amino acid sequence represented by SEQ ID NO:1, and has β1,3-galactosyltransferase activity.

The protein which consists of an amino acid sequence in which at least one amino acid is deleted, substituted, inserted or added, and has β1,3-galactosyltransferase activity can readily be obtained by using a method for introducing site-directed mutagenesis described in, for example, *Molecular Cloning, A Laboratory Manual*, Second Edition, Cold Spring Harbor Laboratory Press (1989) (hereinafter referred to as "*Molecular Cloning*, Second Edition"); *Current Protocols in Molecular Biology*, John Wiley & Sons (1987–1997) (hereinafter referred to as "*Current Protocols in Molecular Biology*"); *Nucleic Acids. Research*, 10, 6487 (1982); *Proc. Natl. Acad. Sci. USA*, 79, 6409 (1982); *Gene*, 34, 315 (1985); *Nucleic Acids. Research*, 13, 4431 (1985); *Proc. Natl. Acad. Sci. USA*, 82, 488 (1985) and the like. For example, the protein can be obtained by introducing mutation(s) to DNA encoding a protein consisting of the amino acid sequence represented by SEQ ID NO:1.

The number of the amino acids which are deleted, substituted, inserted or added is not particularly limited; however, it is such a number that deletion, substitution, insertion or addition can be carried out by a known method such as method for introducing site-directed mutation(s). The number is 1 to several tens, preferably 1 to 20, more preferably 1 to 10, and most preferably 1 to 5.

The deletion, substitution, insertion or addition of at least one amino acid residue in the amino acid sequence represented by SEQ ID NO:1 means that one or at least two amino acids are deleted, substituted, inserted or added at any position in the same sequence. The deletion, substitution, insertion or addition can be carried out in the same amino acid sequence simultaneously. Also, the amino acid residue substituted, inserted or added can be natural or non-natural. The natural amino acid residue includes L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine, and the like.

Herein, examples of amino acid residues which are substituted with each other are shown below. Amino acid residues in the same group can readily be substituted with each other.

Group A:
leucine, isoleucine, norleucine, valine, norvaline, alanine, 2-aminobutanoic acid, methionine, O-methylserine, t-butylglycine, t-butylalanine, cyclohexylalanine;

Group B:
asparatic acid, glutamic acid, isoasparatic acid, isoglutamic acid, 2-aminoadipic acid, 2-aminosuberic acid;

Group C:
asparagine, glutamine;

Group D:
lysine, arginine, ornithine, 2,4-diaminobutanoic acid, 2,3-diaminopropionic acid;

Group E:
proline, 3-hydroxyproline, 4-hydroxyproline;

Group F:
serine, threonine, homoserine;

Group G:
phenylalanine, tyrosine.

Also, in order that the protein of the present invention has β1,3-galactosyltransferase activity, the protein has a homology of preferably at least 60% or more, more preferably 80% or more, and most preferably 95% or more, with the amino acid sequence represented by SEQ ID NO:1.

The identity of an amino acid sequence or a nucleotide sequence can be determined by using the algorithm BLAST by Karlin and Altschl [*Proc. Natl. Acad. Sci. USA*, 90, 5873 (1993)] or FASTA [*Methods Enzymol.*, 183, 63 (1990)]. The programs called BLASTN and BLASTX have developed based on the above algorithm BLAST [*J. Mol. Biol.*, 215, 403 (1990)]. In the case of analyzing a nucleotide sequence by BLASTN based on BLAST, for example, the parameter can be set to score=100, wordlength=12. Also, in the case of analyzing an amino acid sequence by BLASTX based on BLAST, for example, the parameter can be set to score=50, wordlength=3. When BLAST and Gapped BLAST programs are used, a default parameter of each program can be used. The specific analysis methods of using the above programs are known (http://www.ncbi.nlm.nih.gov.).

Any DNA can be used as the DNA of the present invention, so long as it encodes the protein of the present invention. It is preferably a DNA derived from a microorganism, more preferably a DNA derived from a microorganism belonging to the genus *Helicobacter*, and most preferably a DNA derived from *Helicobacter pylori*. Examples include:

(1) a DNA encoding a protein comprising the amino acid sequence represented by SEQ ID NO:1, (2) a DNA comprising the nucleotide sequence represented by SEQ ID NO:2, (3) a DNA encoding a protein which consists of an amino acid sequence in which at least one amino acid is deleted, substituted, inserted or added in the amino acid sequence represented by SEQ ID NO:1, and has β1,3-galactosyltransferase activity, and (4) a DNA which hybridizes with the DNA according to any one of (1) to (3) under stringent conditions and encodes a protein having β1,3-galactosyltransferase activity.

The DNA which is hybridizable under stringent conditions is a DNA obtained by colony hybridization, plaque hybridization, Southern hybridization or the like using, as a probe, a part or a full length of the DNA according to any one of (1) to (3). Specifically, the DNA includes a DNA which can be identified by carrying out hybridization at 65° C. in the presence of 0.7–1.0 mol/l NaCl using a filter on which a DNA prepared from colonies or plaques is immobilized, and then washing the filter with 0.1× to 2×SSC solution (the composition of 1×SSC solution contains 150 mmol/l sodium chloride and 15 mmol/l sodium citrate) at 65° C. The hybridization can be carried out in accordance with a known method described in, for example, *Molecular Cloning*, Second Edition; *Current Protocols in Molecular Biology*; *DNA Cloning 1: Core Techniques, A Practical Approach*, Second Edition, Oxford University (1995) or the like. Specifically, the DNA which is hybridizable includes a DNA having a homology of at least 60% or more, preferably 80% or more, and more preferably 95% or more, with the nucleotide sequence represented by SEQ ID NO:2 when calculated based on the above parameters using above BLAST, FASTA or the like.

(1) Preparation of the DNA of the Present Invention

The full nucleotide sequence of the genomic DNA in *Helicobacter pylori* 26695 was determined [*Nature*, 388, 539 (1997)], and the sequence information of the gene of interest can be obtained by using the genomic DNA sequence database (http://www.ncbi.nlm.nih.gov/Entrez/Genome/org.html, http://www.tigr.org./tdb/).

The DNA encoding the protein of the present invention can be prepared from a microorganism belonging to the genus *Helicobacter*. The microorganism belonging to the genus *Helicobacter* includes *Helicobacter pylori*, and specifically *Helicobacter pylori* NCTC 11637 (ATCC 43504) and the like.

The microorganism belonging to the *Helicobacter pylori* can be cultured by a known method [for example, *Mol Microbiol*, 20, 833 (1996)].

After the culturing, a chromosomal DNA of the microorganism can be isolated and purified by a known method (for example, method described in *Current Protocols in Molecular Biology*).

A DNA fragment containing the DNA of the present invention can be obtained by preparing a primer based on the nucleotide sequence of the genome and then carrying out PCR [*PCR Protocols*, Academic Press (1990)] using the genomic DNA as a template.

Furthermore, the DNA of interest can be obtained according to a hybridization method by using the synthetic DNA designed based on the nucleotide sequence of the genome as a probe.

The nucleotide sequence of the DNA can be determined by inserting the obtained DNA as it is or after digestion with an appropriate restriction enzyme, into a vector according to the usual method, and carrying out analysis by the generally used nucleotide sequence analysis method such as the dideoxy method [*Proc. Natl. Acad. Sci. USA*, 74, 5463 (1977)] or a method comprising the use of an apparatus for nucleotide sequence analysis such as 373A-DNA Sequencer (manufactured by Perkin-Elmer).

Based on the nucleotide sequence thus determined, the DNA of interest can also be prepared by chemical synthesis using, for example, DNA Synthesizer 8905 manufactured by Perceptive Biosystems or the like.

The thus obtained DNA includes a DNA comprising the sequence represented by SEQ ID NO:2.

The vector into which the DNA of the present invention is ligated includes pBluescript KS(+) (manufactured by Stratagene), pDIRECT [*Nucleic Acids Res.*, 18, 6069 (1990)], pCR-Script Amp SK(+) (manufactured by Stratagene), pT7Blue manufactured by Novagen), pCR II (manufactured by Invitrogen), pCR-TRAP (manufactured by Genehunter) and the like.

The microorganism containing the recombinant DNA comprising the DNA comprising the sequence represented by SEQ ID NO:2 includes *Escherichia coli* and the like.

*Escherichia coli* includes *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB 101, *Escherichia coli* No. 49, *Escherichia coli* W3110, *Escherichia coli* NY49, *Escherichia coli* MP347, *Escherichia coli* NM522, *Escherichia coli* ME8415 and the like.

Any method can be used in the introduction method of the recombinant DNA, so long as it is a method for introducing DNA into the host cell. Examples include the method using a calcium ion [*Proc. Natl. Acad. Sci. USA*, 69, 2110 (1972)], the protoplast method (Japanese Published Unexamined Patent Application No. 248394/88), electroporation [*Nucleic Acid Res.*, 16, 6127 (1988)] and the like.

*Escherichia coli* containing the recombinant DNA comprising a DNA comprising the nucleotide sequence represented by SEQ ID NO:2 includes *Escherichia coli* NM522/pGT116.

(2) Preparation of the Protein of the Present invention.

The protein of the present invention can be produced by expressing the DNA of the present invention obtained by the method of (1) in a host cell, for example, as shown below, by using a method described in *Molecular Cloning*, Second Edition, *Current Protocols in Molecular Biology* or the like.

Based on the DNA of the present invention, a DNA fragment of an appropriate length containing a portion which encodes the protein can be prepared, if necessary. In addition, productivity of the protein can be improved by substituting a nucleotide in the nucleotide sequence of the protein-coding region so that it has the most suitable codons for the expression in the host.

A recombinant DNA is prepared by inserting the DNA into a downstream of the promoter of an appropriate expression vector.

A transformant which produces the protein used for the process of the present invention can be obtained by introducing the recombinant DNA into a host cell suitable for the expression vector.

Any bacteria, yeasts, animal cells, insect cells, plant cells and the like can be used as the host cell, so long as it can express the gene of interest.

The expression vectors include those which can replicate autonomously in the above host cell or those which can be integrated into a chromosome and have a promoter at such a position that the DNA of the present invention can be transcribed.

When a procaryote cell such as a bacterial cell is used as the host cell, it is preferred that the recombinant DNA can replicate autonomously in the procaryote cell, and that the recombinant vector contains a promoter, a ribosome binding sequence, the DNA of the present invention and a transcription termination sequence. The vector may further comprise a gene regulating the promoter.

The expression vector includes pHelix1 (manufactured by Roche Diagnostics), pKK233-2 (manufactured by Amersham Pharmacia Biotech), pSE280 (manufactured by Invitrogen), pGEMEX-1 (manufactured by Promega), pQE-8 (manufactured by QIAGEN), pET-3 (manufactured by Novagen), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(+), pBluescript II KS(−) (manufactured by Stratagene), pTrs30 [prepared from Escherichia coli JM109/pTrS30 (FERM BP-5407)], pTrs32 [prepared from Escherichia coli JM109/pTrS32 (FERM BP-5408)], pPAC31 (WO98/12343), pUC19 [Gene, 33, 103 (1985)], pSTV28 (manufactured by Takara Shuzo), pUC118 (manufactured by Takara Shuzo), pPA1 (Japanese Published Unexamined Patent Application No. 233798/88) and the like.

Any promoter can be used, so long as it can function in the host cell. Examples include promoters derived from Escherichia coli, phage and the like, such as trp promoter ($P_{trp}$), lac promoter ($P_{lac}$), $P_L$ promoter, $P_R$ promoter and $P_{SE}$ promoter, SPO1 promoter, SPO2 promoter, penP promoter and the like. Also, artificially designed and modified promoters, such as a promoter in which two $P_{trp}$ are linked in tandem, tac promoter, lacT7 promoter and letI promoter, can be used.

It is preferred to use a plasmid in which the space between Shine-Dalgarno sequence, which is the ribosome binding sequence, and the initiation codon is adjusted to an appropriate distance (for example, 6 to 18 nucleotides).

The transcription termination sequence is not essential for the recombinant DNA of the present invention. However, it is preferred to lie a transcription terminating sequence immediately downstream of the structural gene.

The procaryotes include microorganisms belonging to the genera Escherichia, Serratia, Bacillus, Brevibacterium, Corynebacterium, Microbacterium, Pseudomonas and the like. Examples include Escherichia coli XL1-Blue, Escherichia coli XL2-Blue, Escherichia coli DH1, Escherichia coli NM522, Escherichia coli MC1000, Escherichia coli KY3276, Escherichia coli W1485, Escherichia coli JM109, Escherichia coli HB 101, Escherichia coli No. 49, Escherichia coli W3110, Escherichia coli NY49, Serratia ficaria, Serratia fonticola, Serratia liquefaciens, Serratia marcescens, Bacillus subtilis, Bacillus amyloliquefaciens, Brevibacterium immariophilum ATCC 14068, Brevibacterium saccharolyticum ATCC 14066, Corynebacterium ammoniagenes, Corynebacterium glutamicum ATCC 13032, Corynebacterium glutamicum ATCC 14067, Corynebacterium glutamicum ATCC 13869, Corynebacterium acetoacidophilum ATCC 13870, Microbacterium ammoniaphilum ATCC 15354, Pseudomonas sp. D-0110 and the like.

Introduction of the recombinant DNA can be carried out by any methods for introducing DNA into the above-described host cells, such as the method using a calcium ion [Proc. Natl. Acad. Sci. USA, 69, 2110 (1972)], the protoplast method (Japanese Published Unexamined Patent Application No. 248394/88) and electroporation [Nucleic Acids Res., 16, 6127 (1988)].

When a yeast cell is used as the host cell, the expression vector includes YEp13 (ATCC 37115), YEp24 (ATCC 37051), YCp50 (ATCC 37419), pHS19, pHS15 and the like.

Any promoter can be used so long as it can function in yeast. Examples include PHO5 promoter, PGK promoter, GAP promoter, ADH promoter, gal 1 promoter, gal 10 promoter, a beat shock polypeptide promoter, MFα1 promoter, CUP 1 promoter and the like.

The host cell includes yeast strain belonging to the genera Saccharomyces, Schizosaccharomyces, Kluyveromyces, Trichosporon, Schwanniomyces, Pichia, Candida and the like. Examples include Saccharomyces cerevisiae, Schizosaccharomyces pombe, Kluyveromyces lactis, Trichosporon pullulans, Schwanniomyces alluvius, Pichiapastoris, Candida utilis and the like.

Introduction of the recombinant DNA can be carried out by any of the methods for introducing DNA into yeast, such as electroporation [Methods. Enzymol., 194, 182 (1990)], the spheroplast method [Proc. Natl. Acad. Sci. USA, 81, 4889 (1984)] and the lithium acetate method [J. Bacteriol., 153, 163 (1983)].

When an animal cell is used as the host cell, the expression vector includes pcDNAI and pcDM8 (manufactured by Funakoshi), pAGE107 (Japanese Published Unexamined Patent Application No. 22979/91), pAS3-3 (Japanese Published Unexamined Patent Application No. 227075/90), pCDM8 [Nature, 329, 840 (1987)], pcDNAI/Amp (manufactured by Invitrogen), pREP4 (manufactured by Invitrogen), pAGE103 [J. Biochem., 101, 1307 (1987)], pAGE210, pAMo, pAMoA and the like.

Any promoter can be used, so long as it can function in an animal cell. Examples include a promoter of IE (immediate early) gene of cytomegalovirus (CMV), SV40 early promoter, a metallothionein promoter, a promoter of retrovirus, a heat shock promoter, SRα promoter and the like. Also, the enhancer of the IE gene of human CMV can be used together with the promoter.

The host cell includes mouse myeloma cell, rat myeloma cell, mouse hybridoma cell, human Namalwa cell, Namalwa KJM-1 cell, human fetal kidney cell, human leukemia cell, African grivet kidney cell, Chinese hamster ovary (CHO) cell, HST5637 (Japanese Published Unexamined Patent Application No. 299/88) and the like.

The mouse myeloma cell includes SP2/0, NS0 and the like. The rat myeloma cell includes YB2/0 and the like. The human fetal kidney cell includes HEK293 (ATCC: CRL-1573) and the like. The human leukemia cell includes BALL-1 and the like. The African grivet kidney cell includes COS-1, COS-7 and the like.

Introduction of the recombinant DNA into animal cells can be carried out by any of methods for introducing DNA into animal cells, such as electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], and the method described in *Virology*, 52, 456 (1973).

When an insect cell is used as the host cell, the protein can be produced by a known method described in, for example, *Baculovirus Expression Vectors, A Laboratory Manual*, W.H. Freeman and Company, New York (1992), *Molecular Biology, A Laboratory Manual, Current Protocols in Molecular Biology, Bio/Technology*, 6, 47 (1988) or the like.

Specifically, a recombinant gene transfer vector and baculovirus are co-transfected into an insect cell to obtain a recombinant virus in a supernatant of the culture of its insect cell, and then an insect cell is infected with the resulting recombinant virus to produce the protein.

The transfer vector used in the method includes pVL1392, pVL1393 and pBlueBacIII (all manufactured by Invitrogen), and the like.

The baculovirus includes *Autographa californica* nuclear polyhedrosis virus which infects insects of the family Barathra and the like.

The insect cell includes *Spodoptera frugiperda* ovary cell, *Trichoplusia ni* ovary cell, silkworm ovary-derived culturing cell and the like.

*Spodoptera frugiperda* ovary cell includes Sf9 and Sf21 (*Baculovirus Expression Vectors, A Laboratory Manual*) and the like. *Trichoplusia ni* ovary cell includes High 5 and BTI-TN-5B1-4 (manufactured by Invitrogen) and the like. The cell line derived from silkworm ovary cell includes *Bombyx mori* N4 and the like.

The method for co-transfecting the above transfer vector and the above baculovirus for the preparation of the recombinant virus includes the calcium phosphate method (Japanese Published Unexamined Patent Application No. 227075/90), the lipofection method [*Proc. Natl. Acad. Sci. USA*, 84, 7413 (1987)] and the like.

When a plant cell is used as the host cell, the expression vector includes Ti plasmid, a tobacco mosaic virus vector, and the like.

As the promoter, any promoter can be used, so long as it can function in a plant cell. Examples include 35S promoter of cauliflower mosaic virus (CaMV), rice actin 1 promoter and the like.

The host cell includes a plant cell and the like, such as tobacco, potato, tomato, carrot, soybean, rape, alfalfa, rice, wheat and barley.

Introduction of the recombinant vector is carried out by the method for introducing DNA into a plant cell, such as the *Agrobacterium* method (Japanese Published Unexamined Patent Application No. 140885/84, Japanese Published Unexamined Patent Application No. 70080/85, WO 94/00977), electroporation (Japanese Published Unexamined Patent Application No. 251887/85) and the method using a particle gun (Japanese Patent Nos. 2606856 and 2517813).

When expressed in yeast, an animal cell or an insect cell, a glycosylated or sugar chain-added protein can be obtained.

The protein of the present invention can be produced by culturing the transformant of the present invention thus obtained in a medium to produce and accumulate the protein in the culture, and recovering it from the culture.

Culturing of the transformant of the present invention in a medium is carried out according to the conventional method as used in culturing of the host.

As a medium for culturing the transformant obtained by using, as the host, prokaryote such as *Escherichia coli*, or eukaryote such as yeast, either a natural medium or a synthetic medium may be used, so long as it contains a carbon source, a nitrogen source, an inorganic salt and the like which can be assimilated by the organism and the transformant can be cultured efficiently.

Any carbon source can be used, so long as the organism can assimilate, and it includes carbohydrates, such as glucose, fructose, sucrose, molasses containing them, starch and starch hydrolysate; organic acids, such as acetic acid and propionic acid; alcohols, such as ethanol and propanol; and the like.

The nitrogen source includes ammonia, various ammonium salts of inorganic acids or organic acids, such as ammonium chloride, ammonium sulfate, ammonium acetate and ammonium phosphate; other nitrogen-containing compounds; peptone; meat extract; yeast extract; corn steep liquor; casein hydrolysate; soybean meal and soybean meal hydrolysate; various fermented cells and digested matter thereof; and the like.

The inorganic salt includes potassium dihydrogen phosphate, dipotassium hydrogen phosphate, magnesium phosphate, magnesium sulfate, sodium chloride, ferrous sulfate, manganese sulfate, copper sulfate, calcium carbonate and the like.

Culturing is usually carried out under aerobic conditions by shaking culture, submerged spinner culture under aeration or the like. The culturing temperature is preferably from 15 to 40° C., and the culturing time is generally from 5 hours to 7 days. The pH of the medium is preferably maintained at 3.0 to 9.0 during the culturing. The pH can be adjusted using inorganic or organic acid, an alkali solution, urea, calcium carbonate, ammonia or the like.

Also, antibiotics, such as ampicillin and tetracycline, can be added to the medium during culturing, if necessary.

When a microorganism transformed with an expression vector containing an inducible promoter is cultured, an inducer can be added to the medium, if necessary. For example, isopropyl-β-D-thiogalactopyranoside or the like can be added to the medium when a microorganism transformed with an expression vector containing lac promoter is cultured; or indoleacrylic acid or the like can be added thereto when a microorganism transformed with an expression vector containing trp promoter is cultured.

The medium for culturing a transformant obtained using an animal cell as the host includes generally used RPMI 1640 medium [*The Journal of the American Medical Association*, 199, 519 (1967)], Eagle's MEM medium [*Science*, 122, 501 (1952)], DMEM medium [*Virology*, 8, 396 (1959)], and 199 Medium [*Proceeding of the Society for the Biological Medicine*, 73, 1 (1950)], as well as media to which fetal calf serum or the like has been added to the above media and the like.

Culturing is generally carried out at pH 6 to 8 and at 25 to 40° C. for 1 to 7 days in the presence of 5% $CO_2$ or the like.

Furthermore, if necessary, antibiotics such as kanamycin, penicillin and streptomycin, can be added to the medium during the culturing.

The medium for culturing a transformant obtained using an insect cell as the host includes generally used TNM-FH medium (manufactured by Pharmingen), Sf-900 II SFM (manufactured by Life Technologies), ExCell 400 and ExCell 405 (both manufactured by JRH Biosciences), Grace's Insect Medium [*Nature*, 195, 788 (1962)] and the like.

Culturing is generally carried out at pH 6 to 7 and at 25 to 30° C. for 1 to 5 days or the like.

Furthermore, if necessary, antibiotics such as gentamicin can be added to the medium during the culturing.

A transformant obtained by using a plant cell as the host cell can be used as the cell or after differentiating to a plant cell or organ. The medium used in the culturing of the transformant includes Murashige and Skoog (MS) medium, White medium, media to which a plant hormone, such as auxin or cytokinine, has been added, and the like.

Culturing is carried out generally at a pH 5 to 9 and at 20 to 40° C. for 3 to 60 days.

Also, antibiotics, such as kanamycin and hygromycin, can be added to the medium during the culturing, if necessary.

As described above, the protein can be produced by culturing a transformant derived from a microorganism, animal cell or plant cell containing a recombinant DNA to which the DNA of the present invention has been inserted according to the general culturing method to thereby produce and accumulate the protein, and recovering the protein from the culture.

The process for producing the protein of the present invention includes a method of intracellular expression in a host cell, a method of extracellular secretion from a host cell, or a method of production on an outer membrane of the host cell, and depending on the method selected, the host cell employed or the structure of the protein produced is suitably changed.

When the protein of the present invention is produced in a host cell or on an outer membrane of the host cell, the produced protein can be actively secreted extracellularly according to, for example, the method of Paulson et al. [*J. Biol. Chem.*, 264, 17619 (1989)], the method of Lowe et al. [*Proc. Natl. Acad. Sci. USA*, 86, 8227 (1989); *Genes Develop.*, 4, 1288 (1990)], or the methods described in Japanese Published Unexamined Patent Application No. 336963/93, WO94/23021, and the like.

Specifically, the protein of the present invention can be actively secreted extracellularly by producing it in the form that a signal peptide has been added to the side of N-terminal of a protein containing an active site of the protein of the present invention according to the recombinant DNA technique.

Furthermore, the protein production can be increased utilizing a gene amplification system using a dihydrofolate reductase gene or the like according to the method described in Japanese Published Unexamined Patent Application No. 227075/90.

Moreover, the protein of the present invention can be produced by redifferentiating a gene-introduced animal or plant cell to develop a gene-introduced transgenic animal (transgenic nonhuman animal) or plant (transgenic plant), and using the individual.

When the transformant is the animal individual or plant individual, the protein can be produced by breeding or cultivating it to produce and accumulate the protein, and recovering the protein from the animal individual or plant individual.

The process for producing the protein of the present invention using the animal individual includes a method for producing the protein of the present invention in a nonhuman animal developed by introducing a gene according to a known method [*Am. J. Clin. Nutr.*, 63, 639S (1996), *Am. J. Clin. Nutr*, 63, 627S (1996), *Bio/Technology*, 9, 830 (1991)].

In the animal individual, the protein can be produced by breeding a transgenic nonhuman animal to which the DNA of the present invention has been introduced to produce and accumulate the protein in the animal, and recovering the protein from the animal. The protein produced in the animal is accumulated in milk (Japanese Published Unexamined Patent Application No. 309192/88), egg, and the like. Any promoter can be used, so long as it can function in the animal. Suitable examples include an α-casein promoter, a β-casein promoter, a β-lactoglobulin promoter, a whey acidic protein promoter, and the like, which are specific for mammary glandular cells.

The process for producing the protein of the present invention using the plant individual includes a process for producing the protein by cultivating a transgenic plant to which the DNA encoding the protein of the present invention is introduced by a known method [*Tissue Culture* (Soshiki Baiyo), 20 (1994), *Tissue Culture* (Soshiki Baiyo), 21 (1995), *Trends Biotechnol.*, 15, 45 (1997)] to produce and accumulate the protein in the plant, and recovering the protein from the plant.

The protein produced by the transformant of the present invention can be isolated and purified by using the general method for isolating and purifying an enzyme.

For example, when the protein of the present invention is produced as a soluble product in the host cells, the cells are collected by centrifugation after culturing, suspended in an aqueous buffer, and disrupted using an ultrasonicator, a French press, a Manton Gaulin homogenizer, a Dynomill, or the like to obtain a cell-free extract.

From the supernatant obtained by centrifuging the cell-free extract, a purified product can be obtained by the general method used for isolating and purifying an enzyme, for example, solvent extraction, salting-out using ammonium sulfate or the like, desalting, precipitation using an organic solvent, anion exchange chromatography using a resin such as diethylaminoethyl (DEAE)-Sepharose or DIAION HPA-75 (manufactured by Mitsubishi Chemical), cation exchange chromatography using a resin such as S-Sepharose FF (manufactured by Pharmacia), hydrophobic chromatography using a resin such as butyl sepharose or phenyl sepharose, gel filtration using a molecular sieve, affinity chromatography, chromatofocusing, or electrophoresis such as isoelectronic focusing, alone or in combination thereof.

When the protein is produced as an inclusion body in the host cells, the cells are collected in the same manner, disrupted and centrifuged to recover the protein as the precipitate fraction, and then the inclusion body of the protein is solubilized with a protein-denaturing agent.

The solubilized solution is diluted or dialyzed in a solution free from a protein denaturing agent or a solution having a diluted concentration of a protein denaturing agent in such a degree that the protein is not denatured to thereby constitute the normal tertiary structure of the protein, and then a purified product of the protein can be obtained by a purification/isolation method similar to the above.

When the protein of the present invention or its glycosylated-derivative is secreted out of cells, the protein or its derivative can be collected in the culture supernatant.

Specifically, the culture medium is treated in a manner similar to the above, such as centrifugation to obtain a solubilized fraction, from which a purified product can be obtained using a purification/isolation method similar to the above.

The protein obtained by the above method includes a protein comprising the amino acid sequence represented by SEQ ID NO:1.

Furthermore, the protein of the present invention is produced as a fusion protein with other protein, and can be purified using affinity chromatography using a substance having affinity to the fusion protein. For example, the polypeptide of the present invention is produced as a fusion protein with protein A according to the method of Lowe et al. [*Proc. Natl. Acad. Sci. USA*, 86, 8227 (1989); *Genes Develop.*, 4, 1288 (1990)], or the method described in Japanese Published Unexamined Patent Application No. 336963/93 or WO94/23021, and the fusion protein can be purified by affinity chromatography using immunoglubulin G.

Moreover, the protein of the present invention is produced as a fusion protein with Flag peptide, and the fusion protein can be purified by affinity chromatography using an anti-Flag antibody [*Proc. Natl. Acad. Sci., USA*, 86, 8227 (1989), *Genes Develop.*, 4, 1288 (1990)]. In addition, purification can be carried out by affinity chromatography using the antibody against the polypeptide per se.

Based on the amino acid sequence information of the protein thus obtained, the protein of the present invention can be produced by a chemical synthesis method, such as Fmoc (fluorenylmethyloxycarbonyl) method or tBoc (t-butyloxycarbonyl) method. It can also be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

(3) Preparation of Galactose-containing Complex Carbohydrate

A galactose-containing complex carbohydrate can be produced in an aqueous medium by allowing a culture of the transformant obtained by the culturing described in (2) or a treated product of the culture as an enzyme source, uridine-5'-diphosphogalactose and an acceptor complex carbohydrate to be present in the aqueous medium.

The treated product of culture includes a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells, an enzyme preparation obtained by extracting from the cell, and the like.

The enzyme source used in the production of a galactose-containing complex carbohydrate is used in a concentration of 1 mU/l to 1,000 U/l, preferably 10 mU/l to 100 U/l, when the activity capable of forming 1 μmol of galactose-containing complex carbohydrate at 37° C. in 1 minute is defined as 1 unit (U).

The uridine-5'-diphosphogalactose (hereinafter referred to as "UDP-Gal") obtained by the above method includes purified or partly purified UDP-Gal, and UDP-Gal prepared in the aqueous medium using a microorganism. That is, according to the method described in WO98/12343, using a culture of a microorganism capable of producing UTP from a UTP precursor or a treated product of the culture, a culture of a microorganism capable of producing UDP-Gal from UTP and galactose or a treated product of the culture as enzyme sources, and the enzyme sources, a UTP precursor, a sugar and galactose are allowed to be present in the aqueous medium to thereby produce and accumulate UDP-Gal in the aqueous medium.

Specifically, the UTP precursor includes orotic acid, the microorganism capable of producing UTP includes *Corynebacterium ammoniagenes*, the microorganism capable of producing UDP-Gal from UTP and galactose includes *Escherichia coli* NM522/pNT25/pNT32 (WO98/12343) containing plasmid pNT25 which expresses galT gene [*Nucleic Acid Res.*, 14, 7705 (1986)] and galK gene [*Nucleic Acid Res.*, 13, 1841 (1985)] and plasmid pNT32 which expresses galU gene [*J. Biochem.*, 115, 965 (1994)] and ppa gene [*J. Bacteriol.*, 170, 5901 (1988)].

The aqueous medium used in the production of a galactose-containing complex carbohydrate includes water; a buffer such as a phosphate buffer, a carbonate buffer, an acetate buffer, a borate buffer, a citrate buffer and a tris buffer; alcohol, such as methanol and ethanol; ester such as ethyl acetate; ketone such as acetone; amide such as acetamide; and the like. Also, the culture of the microorganisms used as the enzyme source can be used as an aqueous medium.

In producing a galactose-containing complex carbohydrate, a surfactant or an organic solvent may be added, if necessary. Any surfactant capable of accelerating the formation of a galactose-containing complex carbohydrate can be used as the surfactant. Examples include nonionic surfactants such as polyoxyethylene octadecylamine (e.g., Nymeen S-215, manufactured by Nippon Oil & Fats); cationic surfactants, such as cetyltrimethylammonium bromide and alkyldimethyl benzylammoniumchloride (e.g., Cation F2-40E, manufactured by Nippon Oil & Fats); anionic surfactants such as lauroyl sarcosinate; tertiary amines such as alkyldimethylamine (e.g., Tertiary Amine FB, manufactured by Nippon Oil & Fats); and the like, which are used alone or as a mixture of two or more. The surfactant is used generally in a concentration of 0.1 to 50 g/l. The organic solvent includes xylene, toluene, fatty acid alcohol, acetone, ethyl acetate, and the like, which are used in a concentration of generally 0.1 to 50 ml/l.

The galactose-containing complex carbohydrate production reaction is carried out in an aqueous medium having a pH 5 to 10, preferably pH 6 to 8, at 20 to 50° C. for 1 to 96 hours. In the production reaction, inorganic salts, such as $MnCl_2$ and $MgCl_2$, can be added, if necessary.

The amount of the galactose-containing complex carbohydrate produced in the aqueous medium can be determined, for example, using a carbohydrate analysis system manufactured by Dionex [*Anal. Biochem.*, 189:, 151 (1990)] or the like.

The galactose-containing complex carbohydrate produced in the aqueous medium can be recovered by the ordinary method using activated carbon, an ion exchange resin or the like.

BRIEF EXPLANATION OF THE DRAWING

Symbols in the drawing have the following meanings.

$Amp^r$: ampicillin-resistant gene.

$P_L$: $P_L$ promoter.

cI857: temperature-sensitive repressor gene.

HP0619: gene encoding β1,3-galactosyltransferase derived from *Helicobacter pylori*.

BEST MODE FOR CARRYING OUT THE INVENTION

The present invention is explained based on Examples, but the present invention is not limited to Examples.

EXAMPLE 1

Construction of a Strain in which a Gene Derived from *Helicobacter pylori* is Expressed:

*Helicobacter pylori* NCTC 11637 was cultured by a known method [e.g., *Mol. Microbiol.* 20, 833 (1996)].

After the culturing, a chromosomal DNA of the microorganism was isolated and purified by a method described in *Current Protocols in Molecular Biology*.

Using the DNAs represented by SEQ ID NOs:3 and 4 which had been synthesized using DNA synthesizer 8905 manufactured by Perceptive Biosystems, a fragment containing a DNA corresponding to HPO619 gene of *Helicobacter pylori* 26695 was amplified by the following method.

Using the above synthetic DNAs as primers, PCR was carried out by using the chromosomal DNA of *Helicobacter pylori* NCTC 11637 as a template. PCR was carried out using 40 μl of a reaction solution containing 0.1 μg of the chromosomal DNA, 0.5 μmol/l of each primer, 2.5 units of Pfu DNA polymerase (manufactured by Stratagene), 4 μl of a 10× buffer for Pfu DNA polymerase and 200 μmol/l of each deoxyNTP and repeating 30 times of a reaction step consisting of 1 minute at 94° C., 2 minutes at 42° C. and 3 minutes at 72° C.

After confirming amplification of the fragment of interest by subjecting 1/10 volume of the reaction solution to agarose gel electrophoresis, the remaining reaction solution was mixed with the same volume of TE [10 mmol/l Tris-HCl, 1 mmol/l EDTA (pH 8.0)] saturated phenouchloroform (1 vol/1 vol).

After centrifugation of the mixed solution, two equivalents of cold ethanol was added to the upper layer thus obtained, and the mixture was allowed to stand at −80° C. for 30 minutes. By centrifuging the solution, a DNA precipitate was obtained.

The DNA precipitate was dissolved in 20 μl of TE.

Using 5 μl of the dissolved solution, the DNA fragment was digested with restriction enzymes ClaI and BamHI, the resulting DNA fragments were separated by agarose gel electrophoresis and then a DNA fragment of 1.4 kb was recovered using GeneClean II Kit.

After 0.2 μg of pPAC31 DNA was digested with restriction enzymes ClaI and BamHI, the resulting DNA fragments were separated by agarose gel electrophoresis and then a DNA fragment of 5.5 kb was recovered in the same manner.

Using a ligation kit, the 1.4 kb and 5.5 kb fragments were subjected to a ligation reaction at 16° C. for 16 hours.

Using the ligation reaction solution, *Escherichia coli* NM522 was transformed in accordance with the above known method, and the transformants were spread on LB agar medium [10 g/l bacto tryptone (manufactured by Difco), 10 g/l yeast extract (manufactured by Difco), 5 μl sodium chloride, 15 g/l agarose] containing 50 mg/ml ampicillin and then cultured overnight at 30° C.

Figure 1:
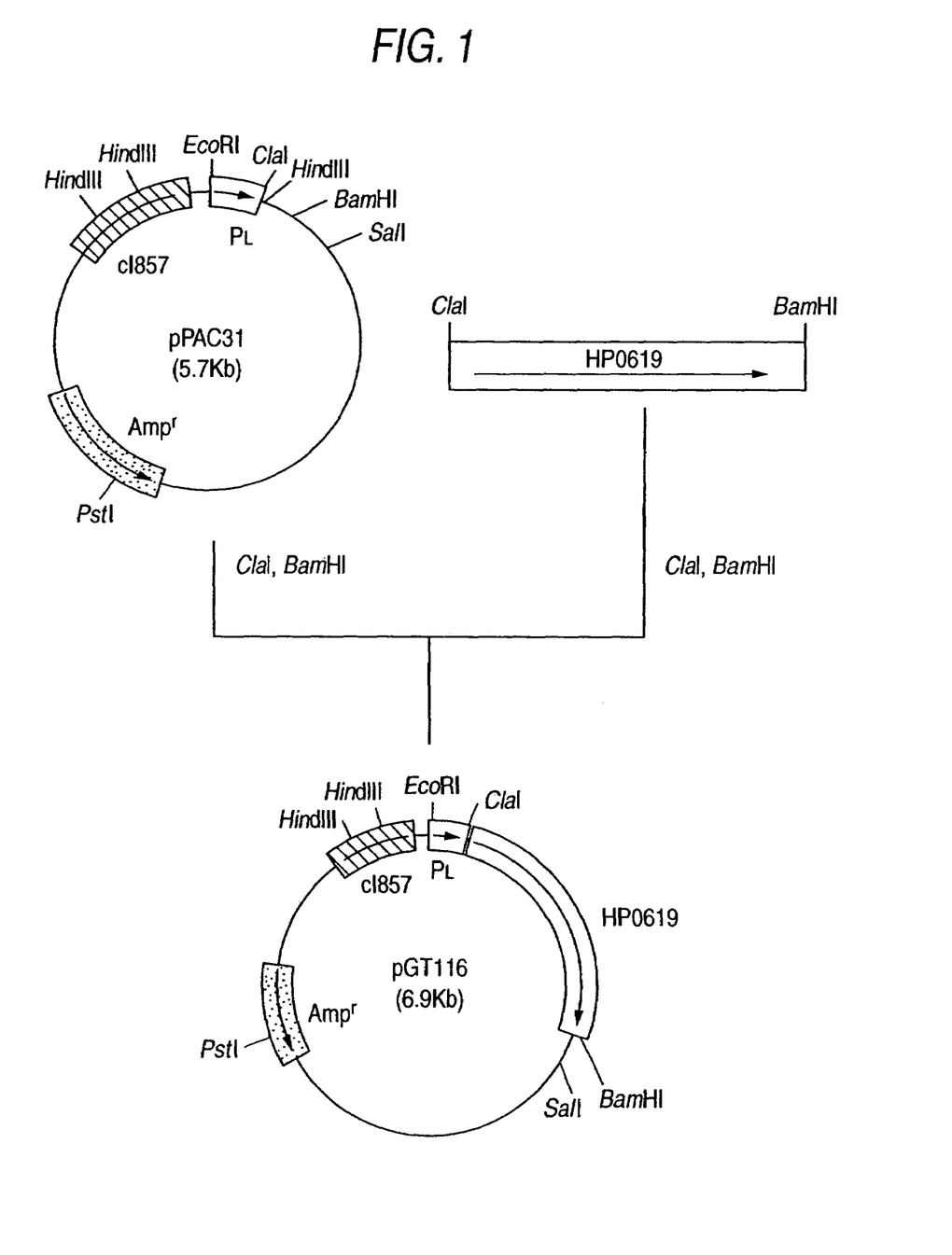
FIG. 1 shows construction steps of 1,3-galactosyltransferase expression plsmid pGT116.

By extracting a plasmid from the grown transformant colonies in accordance with the above known method, an expression plasmid pGT116 was obtained. The structure of the plasmid was confirmed by restriction enzyme digestion (FIG. 1).

EXAMPLE 2

Production of lacto-N-biose (Galβ1,3GlcNAc):

*Escherichia coli* NM522/pGT116 obtained in Example 1 was inoculated into a test tube charged with 8 ml of LB medium containing 50 μg/ml ampicillin and cultured at 28° C. for 17 hours. The culture was inoculated into a test tube charged with 8 ml of LB medium containing 50 μg/ml ampicillin, with an inoculum size of 1%, and cultured at 28° C. for 4 hours and then at 40° C. for 3 hours. Wet cells were obtained by centrifuging 0.1 ml of the culture. The wet cells could be stored at −20° C., if necessary, and it was able to use them by thawing prior to use.

The reaction was carried out at 37° C. for 24 hours in 0.1 ml of a reaction solution composed of the thus obtained wet cells of *Escherichia coli* NM522/pGT116, 50 mmol/l of a citrate buffer (pH 7.0), 10 mmol/l $MnCl_2$, 10 mmol/l GlcNAc, 10 mmol/l UDP-galactose and 4 g/l Nymeen S-215.

After completion of the reaction, the reaction product was analyzed using a carbohydrate analysis system manufactured by Dionex (DX-500) under the following analyzing conditions to confirm that 0.6 mmol/l (221 mg/l) lacto-N-biose was produced and accumulated in the reaction solution.

Analyzing Conditions:

Column: CarboPAC PA10

Eluent: A; $H_2O$, B; 500 mmol/l NaOH

Gradient: Concentration of the eluent B at 0 minute is adjusted to 8% and increased to 20% spending 21 minutes.

Detector: Pulsed amperometry detector

EXAMPLE 3

Production of lacto-N-tetraose (Galβ1,3GlcNAcβ1,3Galβ1,4Glc)(1)

*Escherichia coli* NM522/pGT116 obtained in Example 1 was cultured by the method described in Example 2. Wet cells were obtained by centrifuging 0.1 ml of the culture. The wet cells could be stored at −20° C., if necessary, and it was able to use them by thawing prior to use.

The reaction was carried out at 37° C. for 24 hours in 0.1 ml of a reaction solution composed of the obtained wet cells of *Escherichia coli* NM522/pGT116, 50 mmol/l of a citrate buffer (pH 7.0), 10 mmol/l $MnCl_2$, 10 mmol/l GlcNAcβ1,3Galβ1,4Glc, 10 mmol/l UDP-galactose and 4 g/l Nymeen S-215.

After completion of the reaction, the reaction product was analyzed using a carbohydrate analysis system manufactured by Dionex (DX-500) under the analyzing conditions described in Example 2 to confirm that 4.3 mmol/l (3.1 g/l) lacto-N-tetraose was produced and accumulated in the reaction solution.

EXAMPLE 4

Production of para-lacto-N-hexaose (Galβ1,3GlcNAcβ1,3Galβ1,4GlcNAcβ1,3Galβ1,4Glc):

*Escherichia coli* NM522/pGT116 obtained in Example 1 was cultured by the method described in Example 2. Wet cells were obtained by centrifuging 0.1 ml of the culture. The wet cells could be stored at −20° C., if necessary, and it was able to use them by thawing prior to use.

The reaction was carried out at 37° C. for 10 hours in 0.1 ml of a reaction solution composed of the obtained wet cells of *Escherichia coli* NM522/pGT116, 50 mmol/l of a citrate buffer (pH 7.0), 10 mmol/l MnCl$_2$, 10 mmol/l GlcNAcβ1, 3Galβ1,4GlcNAcβ1,3Galβ1,4Glc, 10 mmol/l UDP-galactose and 4 g/l Nymeen S-215.

After completion of the reaction, the reaction product was analyzed using a carbohydrate analysis system manufactured by Dionex (DX-500) under the analyzing conditions described in Example 2 to confirm that 2.2 mmol/l (2.4 g/l) p-lacto-N-hexaose was produced and accumulated in the reaction solution.

EXAMPLE 5

Production of lacto-N-tetraose (Galβ1,3GlcNAcβ1,3Galβ1, 4Glc) (2):

*Escherichia coli* NM522/pGT116 obtained in Example 1 was inoculated on 125 ml of LB medium [10 g/l Bacto-Tryptone (manufactured by Difco), 10 g/l yeast extract (manufactured by Difco), 5 g/l sodium chloride (pH 7.3)] containing 50 μg/ml ampicillin in a one-liter capacity baffle-equipped conical flask and cultured at 28° C. for 17 hours at 220 rpm. After 125 ml of the culture was inoculated on 2.5 liters of TB medium [10 g/l glucose, 12 g/l Bacto-Tryptone (manufactured by Difco), 24 g/l yeast extract (manufactured by Difco), 2.3 μl KH$_2$PO$_4$, 12.5 g/l K$_2$HPO$_4$ (pH not adjusted)] containing 50 μg/ml ampicillin in a five-liter capacity jar fermentor, and the mixture was cultured at 30° C. for 4 hours and then at 40° C. for 3 hours at 600 rpm and 2.5 liter/min aeration. During the culturing, the pH of the medium was adjusted at 7.0 using 28% aqueous ammonia, and glucose was added, if necessary. Wet cells were obtained by centrifuging the culture. The wet cells could be stored at −20° C., if necessary, and it was able to use them by thawing prior to use.

*Escherichia coli* NM522/pNT25/pNT32 obtained by a known method [*Nat. Biotechnol.*, 16, 847 (1998)] was inoculated on 125 ml of LB medium containing 50 μg/ml ampicillin and 10 μg/ml chloramphenicol in a one-liter capacity baffle-equipped conical flask and cultured at 28° C. for 17 hours at 220 rpm. After 125 ml of the culture was inoculated on 2.5 liters of TB medium containing 50 μg/ml ampicillin and 10 μg/ml chloramphenicol in a five-liter capacity jar fermentor, the mixture was cultured at 30° C. for 4 hours and then at 40° C. for 3 hours at 600 rpm and 2.5 liter/min aeration. During the culturing, the pH of the medium was adjusted at 7.0 using 28% aqueous ammonia, and glucose was added, if necessary. Wet cells were obtained by centrifuging the culture. The wet cells could be stored at −20° C., if necessary, and it was able to use them by thawing prior to use.

In a 300 ml capacity baffle-equipped conical flask, *Corynebacterium ammoniagenes* ATCC 21170 was inoculated into 25 ml of a liquid medium comprising a composition of 50 g/l glucose, 10 g/l polypeptone (manufactured by Nippon Pharmaceutical), 10 g/l yeast extract (manufactured by Oriental Yeast), 5 g/l urea, 5 g/l (NH$_4$)$_2$SO$_4$, 1 g/l KH$_2$PO$_4$, 3 g/l K$_2$HPO$_4$, 1 g/l MgSO$_4$.7H$_2$O, 0.1 g/l CaCl$_2$.2H$_2$O, 10 mg/l FeSO$_4$.7H$_2$O, 10 mg/l ZnSO$_4$.7H$_2$O, 20 mg/l MnSO$_4$.6H$_2$O, 20 mg/l L-cysteine, 10 mg/l calcium D-pantothenate, 5 mg/l vitamin B1, 5 mg/l nicotinic acid and 30 μg/ml biotin (adjusted to pH 7.2 with NaOH), followed by culturing at 28° C. for 24 hours at 220 rpm.

In a two-liter capacity baffle-equipped conical flask, 20 ml of the culture was inoculated into 250 ml of a liquid medium having the same composition described above, the mixture was cultured at 28° C. for 24 hours at 220 rpm. The thus obtained culture was used as a seed culture medium.

In a five-liter capacity jar fermentor, 250 ml of the seed culture medium was inoculated into 2.25 liters of a liquid medium comprising a composition of 150 g/l glucose, 5 g/l meat extract (manufactured by Kyokuto Pharmaceutical Industrial), 10 g/l KH$_2$PO$_4$, 10 g/l K$_2$HPO$_4$, 10 g/l MgSO$_4$.7H$_2$O, 0.1 g/l CaCl$_2$.2H$_2$O, 20 mg/l FeSO$_4$.7H$_2$O, 10 mg/l ZnSO$_4$.7H$_2$O, 20 mg/l MnSO$_4$.4–6H$_2$O (separate sterilization), 15 mg/l β-alanine (separate sterilization), 20 mg/l L-cysteine, 5 mg/l vitamin B1 (separate sterilization), 100 mg/ml biotin and 2 g/l urea (adjusted to pH 7.2 with NaOH), the mixture was cultured at 32° C. for 24 hours at 600 rpm and 2.5 liter/min aeration. During the culturing, the pH of the medium was adjusted at 6.8 using 28% aqueous ammonia.

Wet cells were obtained by centrifuging the culture. The wet cells could be stored at −20° C., if necessary, and it was able to use them by thawing prior to use.

After 30 ml of a reaction solution comprising a composition of 50 g/l of wet cells of *Escherichia coli* NM522/pGT116, 50 g/l of wet cells of *Escherichia coli* NM522/pNT25/pNT32, 150 g/l of wet cells of *Corynebacterium ammoniagenes* ATCC 21170, 50 g/l galactose, 100 g/l GlcNAcβ1,3Galβ1,4Glc, 50 g/l fructose, 5 g/l orotic acid, 5 g/l KH$_2$PO$_4$, 20 g/l K$_2$HPO$_4$, 5 g/l MgSO$_4$.7H$_2$O, 4 g/l Nymeen S-215 and 10 ml/l of xylene was put into a 200 ml capacity beaker, and the reaction solution was stirred (900 rpm) using a magnetic stirrer to carry out the reaction at 32° C. for 24 hours. During the reaction, pH of the reaction solution was kept at 7.2 using 5 mol/l of NaOH, and fructose and KH$_2$PO$_4$ were added, if necessary.

After completion of the reaction, the reaction product was analyzed by the method described in Example 2 to confirm that 61 g/l lacto-N-tetraose was produced and accumulated in the reaction solution.

INDUSTRIAL APPLICABILITY

According to the present invention, a protein having β1,3-galactosyltrasnferase activity can be produced in a large amount. Also, a galactose-containing complex carbohydrate can be produced efficiently by using the enzyme.

Free Text of Sequence Listing:
SEQ ID NO:3—Description of artificial sequence: Synthetic DNA
SEQ ID NO:4—Description of artificial sequence: Synthetic DNA

The invention claimed is:

1. An isolated protein comprising the amino acid sequence represented by SEQ ID NO:1.

2. An isolated protein which consists of an amino acid sequence in which up to 20 amino acids are deleted, substituted, inserted or added in the amino acid sequence of SEQ ID NO: 1, and has β1,3-galactosyltransferase activity.

3. An isolated protein which has a homology of at least 95% with a protein consisting of the amino acid sequence represented by SEQ ID NO:1, and has β1,3-galactosyltransferase activity.

4. An isolated process for producing a galactose-containing complex carbohydrate, which comprises the steps of:
allowing (i) a culture of a transformant containing a recombinant DNA encoding a protein comprising SEQ ID NO:1, or a protein which has a homology of at least 95% with a protein consisting of the amino acid sequence of SEQ ID NO:1 and which has β1,3-galactosyltransferase activity, or a treated product of said culture as an enzyme source, (ii) uridine-5'-diphosphogalactose and (iii) an acceptor complex carbohydrate to be present in an aqueous medium to produce and accumulate the galactose-containing complex carbohydrate in the aqueous medium, and
recovering the galactose-containing complex carbohydrate from the aqueous medium,
wherein the treated product of the culture is selected from the group consisting of a concentrated product of the culture, a dried product of the culture, cells obtained by centrifuging the culture, a dried product of the cells, a freeze-dried product of the cells, a surfactant-treated product of the cells, and wherein the treated product of the culture has β1,3-galactosyltransferase activity.

5. The process according to claim 4, wherein the recombinant DNA comprises SEQ ID NO:2.

6. A process for producing a galactose-containing complex carbohydrate, which comprises the steps of: allowing (i) a culture of a transformant containing a recombinant DNA which hybridizes with a DNA sequence consisting of nucleotide sequence of SEQ ID NO: 2 under stringent conditions, and which encodes a protein having β1,3-galactosyltransferase activity, or a treated product of said culture as an enzyme source, (ii) uridine-5'-diphosphogalactose and (iii) an acceptor complex carbohydrate to be present in an aqueous medium to produce and accumulate the galactose-containing complex carbohydrate in the aqueous medium, and recovering the galactose-containing complex carbohydrate from the aqueous medium,
wherein the stringent conditions comprise hybridization at 65° C. in the presence of 0.7–1.0 mol/l NaCl using a filter bearing immobilized DNA prepared from colonies or plaques, and then washing the filter with 0.1× SSC solution at 65° C., and
wherein the treated product of the culture is selected from the group consisting of a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells and an enzyme preparation obtained by extracting from the cells, and wherein the treated product of the culture has β1,3-galactosyltransferase activity.

7. The process according to any one of claims 4, 5 or 6, wherein the acceptor complex carbohydrate is a complex carbohydrate comprising an oligosaccharide having N-acetylglucosamine in its non-reducing terminal.

8. The process according to claim 7, wherein the oligosaccharide having N-acetylglucosamine in its non-reducing terminal is selected from the group consisting of GlcNAc, GlcNAcβ1,3Galβ1,4Glc and GlcNAcβ1,3Galβ1,4GlcNAcβ1,3Galβ1,4Glc.

9. The process according to any one of claims 4, 5 or 6, wherein the galactose-containing complex carbohydrate is selected from the group consisting of lacto-N-biose (Galβ1,3GlcNAc), lacto-N-tetraose (Galβ1,3GlcNAcβ1,3Galβ1,4Glc) and paralacto-N-hexaose (Galβ1,3GlcNAcβ1,3Galβ1,4GlcNAcβ1,3Galβ1,4Glc).

10. The process according to any one of claims 4, 5 or 6, wherein the transformant is obtained by using a microorganism as a host cell.

11. The process according to claim 8, wherein the microorganism is *Escherichia*.

12. The process according to claim 9, wherein the microorganism is *Escherichia*.

* * * * *

UNITED STATES PATENT AND TRADEMARK OFFICE
CERTIFICATE OF CORRECTION

PATENT NO. : 7,189,550 B2
APPLICATION NO. : 11/227177
DATED : March 13, 2007
INVENTOR(S) : Tetsuo Endo et al.

It is certified that error appears in the above-identified patent and that said Letters Patent is hereby corrected as shown below:

ON THE TITLE PAGE [56] REFERENCES CITED:

Other Publications,
in "Appelmelk et al." (first occurrence) "H typeI" should read --Type I--;
"Appelmelk et al.," (second occurrence) should be deleted;
In "Tomb, et al;", "pylori"," should read --Pylori",--; and
In "Shib S. Basu et al.,", "Biochmca" should read --Biochemica--.

COLUMN 2:

Line 46, "(5)." should read --(5)--.

COLUMN 13:

Line 14, "immunoglubulin" should read --immunoglobulin--.

COLUMN 14:

Line 49, "189:," should read --189,--; and
Line 60, "plsmid" should read --plasmid--.

COLUMN 15:

Line 9, "Strain" should read --strain-- and "Gene Derived" should read --gene derived--; and
Line 10, "Expressed:" should read --expressed:--.

COLUMN 18:

Line 48, "β1,3-galactosyltrasnferase" should read --β1,3-galactosyltransferase--.

COLUMN 25:

Line 30, "An isolated" should read --A--;
Line 50, "cells, and wherein" should read --cells, an ultrasonic-treated product of the cells, a mechanically disrupted product of the cells, a solvent-treated product of the cells, and enzyme-treated product of the cells, a protein fraction of the cells, an immobilized product of the cells and an enzyme preparation obtained by extracting from the cells, and wherein--; and

UNITED STATES PATENT AND TRADEMARK OFFICE
CERTIFICATE OF CORRECTION

| | | |
|---|---|---|
| PATENT NO. | : 7,189,550 B2 | |
| APPLICATION NO. | : 11/227177 | |
| DATED | : March 13, 2007 | |
| INVENTOR(S) | : Tetsuo Endo et al. | |

It is certified that error appears in the above-identified patent and that said Letters Patent is hereby corrected as shown below:

<u>COLUMN 25</u>:

Line 57, "a DNA" should read --the full length DNA--.

Signed and Sealed this

Eleventh Day of September, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 481

<212> TYPE: PRT
<213> ORGANISM: Helicobacter pylori

<400> SEQUENCE: 1

```
Met Ile Ser Val Tyr Ile Ile Ser Leu Lys Glu Ser Gln Arg Arg Leu
  1               5                  10                  15

Asp Thr Glu Lys Leu Val Leu Glu Ser Asn Glu Lys Phe Lys Gly Arg
             20                  25                  30

Cys Val Phe Gln Ile Phe Asp Ala Ile Ser Pro Lys His Glu Asp Phe
         35                  40                  45

Glu Lys Leu Leu Gln Glu Leu Tyr Asp Ser Ser Asn Leu Leu Lys Ser
     50                  55                  60

Asp Trp Phe His Ser Asp Tyr Cys Tyr Gln Glu Leu Leu Pro Gln Glu
 65                  70                  75                  80

Phe Gly Cys Tyr Leu Ser His Tyr Leu Leu Trp Lys Glu Cys Val Lys
                 85                  90                  95

Thr Asn Gln Pro Val Val Ile Leu Glu Asp Asp Ile Ala Leu Glu Ser
            100                 105                 110

Asn Phe Met Gln Ala Leu Glu Asp Cys Leu Lys Ser Pro Phe Asp Phe
        115                 120                 125

Val Arg Leu Tyr Gly His Tyr Trp Gly Gly His Lys Thr Asn Leu Cys
    130                 135                 140

Ala Leu Pro Ile Tyr Thr Glu Asn Glu Asn Glu Val Glu Val Pro
145                 150                 155                 160

Met Glu Asn His Ala Glu Thr Glu Ala Ser Met Glu Lys Thr Pro Ile
                165                 170                 175

Glu Asn His Glu Val Thr Pro Pro Pro Asn Pro Thr Gln Asp Ala
            180                 185                 190

Gln Gln Asp Cys Ile Ile Glu Thr Gln Gln Asp Pro Lys Glu Leu Ser
        195                 200                 205

Glu Pro Cys Lys Ile Ala Pro Gln Lys Thr Ser Phe Asn Pro Val Val
    210                 215                 220

Phe Arg Lys Ile Lys Arg Lys Leu Asn Arg Phe Ile Gly Asn Ile Leu
225                 230                 235                 240

Ala Arg Thr Glu Val Tyr Lys Asn Leu Val Ser Lys Tyr Asp Glu Leu
                245                 250                 255

Thr Gly Lys Tyr Asp Glu Leu Thr Gly Lys Tyr Asp Glu Leu Thr Gly
            260                 265                 270

Lys Tyr Asp Glu Leu Thr Gly Lys Tyr Asp Glu Leu Thr Gly Lys Tyr
        275                 280                 285

Asp Glu Leu Thr Gly Lys Tyr Asp Glu Leu Thr Gly Lys Tyr Asp Glu
    290                 295                 300

Leu Thr Gly Lys Tyr Asp Glu Leu Thr Gly Lys Tyr Asp Glu Leu Thr
305                 310                 315                 320

Gly Lys Tyr Asp Glu Leu Thr Gly Lys Tyr Glu Ser Leu Leu Ala Lys
                325                 330                 335

Glu Val Asn Ile Lys Glu Thr Phe Trp Glu Ser Arg Ala Asp Ser Glu
            340                 345                 350

Lys Glu Ala Leu Phe Leu Glu His Phe Tyr Leu Thr Ser Val Tyr Val
        355                 360                 365

Ala Thr Thr Ala Gly Tyr Tyr Leu Thr Pro Lys Gly Ala Lys Thr Phe
    370                 375                 380

Ile Glu Ala Thr Glu Arg Phe Lys Ile Ile Glu Pro Val Asp Met Phe
385                 390                 395                 400
```

```
Ile Asn Asn Pro Thr Tyr His Asp Val Ala Asn Phe Thr Tyr Leu Pro
            405                 410                 415

Cys Pro Val Ser Leu Asn Lys His Ala Phe Asn Ser Thr Ile Gln Asn
            420                 425                 430

Ala Lys Lys Pro Asp Ile Ser Leu Lys Pro Pro Lys Lys Ser Tyr Phe
            435                 440                 445

Asp Asn Leu Phe Tyr His Lys Phe Asn Ala Gln Lys Cys Leu Lys Ala
            450                 455                 460

Phe His Lys Tyr Ser Lys Gln Tyr Ala Pro Leu Lys Thr Pro Lys Glu
465                 470                 475                 480

Val

<210> SEQ ID NO 2
<211> LENGTH: 1443
<212> TYPE: DNA
<213> ORGANISM: Helicobacter pylori

<400> SEQUENCE: 2
```

| | | | | | | | | | | | | | | | | |
|---|---|---|---|---|---|---|---|---|---|---|---|---|---|---|---|---|
| atg | att | tct | gtt | tat | atc | att | tct | tta | aaa | gaa | agt | caa | agg | cgt | ttg | 48 |
| Met | Ile | Ser | Val | Tyr | Ile | Ile | Ser | Leu | Lys | Glu | Ser | Gln | Arg | Arg | Leu | |
| 1 | | | | 5 | | | | | 10 | | | | | 15 | | |

```
gat act gaa aaa ctc gtt tta gaa tcc aat gaa aag ttt aaa ggc cgt    96
Asp Thr Glu Lys Leu Val Leu Glu Ser Asn Glu Lys Phe Lys Gly Arg
             20                  25                  30 tgc gtt ttt caa atc ttt gac gct att agc ccc aaa cac gaa gat ttt   144
Cys Val Phe Gln Ile Phe Asp Ala Ile Ser Pro Lys His Glu Asp Phe
         35                  40                  45 gaa aaa tta ctt caa gag ctt tat gat tct tca aat ttg tta aaa tcc   192
Glu Lys Leu Leu Gln Glu Leu Tyr Asp Ser Ser Asn Leu Leu Lys Ser
 50                  55                  60 gat tgg ttc cat tct gat tat tgt tat caa gaa tta ttg ccc caa gaa   240
Asp Trp Phe His Ser Asp Tyr Cys Tyr Gln Glu Leu Leu Pro Gln Glu
 65                  70                  75                  80 ttt ggg tgc tat tta agc cat tat ctt ttg tgg aaa gaa tgc gtc aaa   288
Phe Gly Cys Tyr Leu Ser His Tyr Leu Leu Trp Lys Glu Cys Val Lys
                 85                  90                  95 aca aac caa ccg gtc gtt att tta gaa gat gat ata gcc tta gag tct   336
Thr Asn Gln Pro Val Val Ile Leu Glu Asp Asp Ile Ala Leu Glu Ser
            100                 105                 110 aat ttc atg caa gcc tta gaa gat tgc ttg aaa agc cct ttt gat ttt   384
Asn Phe Met Gln Ala Leu Glu Asp Cys Leu Lys Ser Pro Phe Asp Phe
        115                 120                 125 gtg aga ctc tac ggg cat tat tgg gga ggc cat aaa acc aat ttg tgc   432
Val Arg Leu Tyr Gly His Tyr Trp Gly Gly His Lys Thr Asn Leu Cys
    130                 135                 140 gct ctc cct att tat aca gag aat gaa aat gaa gag gtt gaa gtg cct   480
Ala Leu Pro Ile Tyr Thr Glu Asn Glu Asn Glu Glu Val Glu Val Pro
145                 150                 155                 160 atg gaa aat cat gca gag acc gaa gcg tct atg gaa aaa acg cct att   528
Met Glu Asn His Ala Glu Thr Glu Ala Ser Met Glu Lys Thr Pro Ile
                165                 170                 175 gaa aac cat gaa gtt acc ccc ccc ccc aat ccc aca caa gat gca       576
Glu Asn His Glu Val Thr Pro Pro Pro Pro Asn Pro Thr Gln Asp Ala
            180                 185                 190 caa caa gat tgt att att gaa acg caa caa gac ccc aaa gaa cta tct   624
Gln Gln Asp Cys Ile Ile Glu Thr Gln Gln Asp Pro Lys Glu Leu Ser
        195                 200                 205 gag cct tgc aaa ata gcg ccc caa aaa acc tct ttt aat cca gtg gtt   672
```

```
                                                    -continued

Glu Pro Cys Lys Ile Ala Pro Gln Lys Thr Ser Phe Asn Pro Val Val
    210             215                 220 ttt aga aaa att aaa aga aaa ctc aac cgc ttc att gga aat att tta      720
Phe Arg Lys Ile Lys Arg Lys Leu Asn Arg Phe Ile Gly Asn Ile Leu
225             230                 235                 240 gct cgg aca gaa gtg tat aaa aat ctc gta tca aaa tac gat gaa ctc      768
Ala Arg Thr Glu Val Tyr Lys Asn Leu Val Ser Lys Tyr Asp Glu Leu
                245                 250                 255 aca gga aaa tac gat gaa ctc aca gga aaa tac gat gaa ctc aca gga      816
Thr Gly Lys Tyr Asp Glu Leu Thr Gly Lys Tyr Asp Glu Leu Thr Gly
            260                 265                 270 aaa tac gat gaa ctc aca gga aaa tac gat gaa ctc aca gga aaa tac      864
Lys Tyr Asp Glu Leu Thr Gly Lys Tyr Asp Glu Leu Thr Gly Lys Tyr
        275                 280                 285 gat gaa ctc aca gga aaa tac gat gaa ctc aca gga aaa tac gat gaa      912
Asp Glu Leu Thr Gly Lys Tyr Asp Glu Leu Thr Gly Lys Tyr Asp Glu
    290                 295                 300 ctc aca gga aaa tac gat gaa ctc aca gga aaa tac gat gaa ctc aca      960
Leu Thr Gly Lys Tyr Asp Glu Leu Thr Gly Lys Tyr Asp Glu Leu Thr
305                 310                 315                 320 gga aaa tac gat gaa ctc aca gga aaa tac gaa tcc tta ttg gca aaa     1008
Gly Lys Tyr Asp Glu Leu Thr Gly Lys Tyr Glu Ser Leu Leu Ala Lys
                325                 330                 335 gag gta aac atc aaa gag act ttt tgg gaa tct cgt gct gat agc gaa     1056
Glu Val Asn Ile Lys Glu Thr Phe Trp Glu Ser Arg Ala Asp Ser Glu
            340                 345                 350 aaa gaa gcg cta ttt tta gag cat ttt tac ctc acc agc gtg tat gtg     1104
Lys Glu Ala Leu Phe Leu Glu His Phe Tyr Leu Thr Ser Val Tyr Val
        355                 360                 365 gct act acg gca ggc tac tac ctc acg cct aag ggc gct aaa acc ttt     1152
Ala Thr Thr Ala Gly Tyr Tyr Leu Thr Pro Lys Gly Ala Lys Thr Phe
    370                 375                 380 ata gaa gcc acg gag cgt ttt aaa atc ata gag ccg gtg gat atg ttc     1200
Ile Glu Ala Thr Glu Arg Phe Lys Ile Ile Glu Pro Val Asp Met Phe
385                 390                 395                 400 ata aac aac ccc act tac cat gat gtg gct aat ttt acc tat ttg cct     1248
Ile Asn Asn Pro Thr Tyr His Asp Val Ala Asn Phe Thr Tyr Leu Pro
                405                 410                 415 tgc cct gtt tct tta aac aag cat gct ttc aat agc acc att caa aat     1296
Cys Pro Val Ser Leu Asn Lys His Ala Phe Asn Ser Thr Ile Gln Asn
            420                 425                 430 gca aaa aag cct gac att tca tta aag cct cct aaa aaa tct tat ttt     1344
Ala Lys Lys Pro Asp Ile Ser Leu Lys Pro Pro Lys Lys Ser Tyr Phe
        435                 440                 445 gat aat ctt ttt tat cat aaa ttc aac gct caa aag tgc tta aaa gcc     1392
Asp Asn Leu Phe Tyr His Lys Phe Asn Ala Gln Lys Cys Leu Lys Ala
    450                 455                 460 ttt cac aaa tac agc aaa caa tac gct cct tta aaa acc cct aaa gag     1440
Phe His Lys Tyr Ser Lys Gln Tyr Ala Pro Leu Lys Thr Pro Lys Glu
465                 470                 475                 480 gtt                                                                   1443
Val

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA
```

```
<400> SEQUENCE: 3
gagaatcgat atgatttctg tttatatcat ttct                              34

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
acatggatcc cgctcttttt aaacctcttt aggg                              34
```